US010779811B2

United States Patent
Patel et al.

(10) Patent No.: US 10,779,811 B2
(45) Date of Patent: Sep. 22, 2020

(54) BONE ANCHOR HAVING IMPROVED FIXATION STRENGTH

(71) Applicant: SMITH & NEPHEW, INC., Memphis, TN (US)

(72) Inventors: Nehal Navinbhai Patel, Boston, MA (US); Mark Edwin Housman, North Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 250 days.

(21) Appl. No.: 14/567,400

(22) Filed: Dec. 11, 2014

(65) Prior Publication Data

US 2016/0166245 A1 Jun. 16, 2016

(51) Int. Cl.
*A61B 17/04* (2006.01)
*A61B 17/16* (2006.01)

(52) U.S. Cl.
CPC ...... *A61B 17/0401* (2013.01); *A61B 17/1615* (2013.01); *A61B 2017/0403* (2013.01); *A61B 2017/0409* (2013.01); *A61B 2017/0412* (2013.01); *A61B 2017/0414* (2013.01); *A61B 2017/0445* (2013.01); *A61B 2017/0456* (2013.01)

(58) Field of Classification Search
CPC .... A61B 2017/0403; A61B 2017/0414; A61B 2017/0427; A61B 17/0401
See application file for complete search history.

(56) References Cited

U.S. PATENT DOCUMENTS

| 5,505,735 A | 4/1996 | Li |
| 5,522,843 A | 6/1996 | Zang |
| 5,733,307 A | 3/1998 | Dinsdale |
| 5,948,000 A | 9/1999 | Larsen et al. |
| 6,508,830 B2 | 1/2003 | Steiner |
| 7,217,279 B2 | 5/2007 | Reese |
| 7,320,701 B2 | 1/2008 | Haut et al. |
| 7,914,539 B2 | 3/2011 | Stone et al. |
| 8,409,251 B2 | 4/2013 | Cooper et al. |

(Continued)

FOREIGN PATENT DOCUMENTS

| WO | 97/29693 A1 | 8/1997 |
| WO | 00/30552 A1 | 6/2000 |

(Continued)

OTHER PUBLICATIONS

Suture anchor BIORAPTOR(TM), downloaded from www.medicalexpo.com on Oct. 18, 2013.

(Continued)

*Primary Examiner* — Samuel S Hanna
(74) *Attorney, Agent, or Firm* — Burns & Levinson, LLP; Joseph M. Maraia

(57) ABSTRACT

Bone anchors having improved fixation are discussed. The bone anchors include an anchor body and radially protruding ribs that extend approximately parallel to a longitudinal axis of the bone anchor. A leading distal edge of each rib may be configured in a tapered "knife-edge" configuration. Such ribs may mitigate the plow-out effect, preserving contact between the ribs and the surrounding bone along the length of the anchor. Furthermore, such ribs provide increased surface area, improving fixation strength.

25 Claims, 11 Drawing Sheets

(56) References Cited

U.S. PATENT DOCUMENTS

| | | | |
|---|---|---|---|
| 2005/0107828 A1* | 5/2005 | Reese | A61B 17/0401 |
| | | | 606/232 |
| 2005/0149024 A1* | 7/2005 | Ferrante | A61B 17/164 |
| | | | 606/62 |
| 2007/0073299 A1 | 3/2007 | Dreyfuss et al. | |
| 2007/0118229 A1* | 5/2007 | Bergin | A61F 2/30734 |
| | | | 623/23.31 |
| 2007/0198017 A1 | 8/2007 | Tschakaloff et al. | |
| 2008/0109038 A1 | 5/2008 | Steiner et al. | |
| 2008/0167660 A1 | 7/2008 | Moreau et al. | |
| 2009/0076544 A1 | 3/2009 | DiMatteo et al. | |
| 2009/0082806 A1 | 3/2009 | West, Jr. et al. | |
| 2009/0149856 A1* | 6/2009 | Paakinaho | A61L 31/148 |
| | | | 606/60 |
| 2010/0217266 A1* | 8/2010 | Helevirta | A61B 17/0401 |
| | | | 606/76 |
| 2010/0029273 A1 | 11/2010 | Hirotsuka et al. | |
| 2012/0203340 A1 | 8/2012 | Choinski et al. | |
| 2012/0245631 A1 | 9/2012 | Lunn et al. | |
| 2012/0296345 A1* | 11/2012 | Wack | A61B 17/0483 |
| | | | 606/139 |
| 2013/0023929 A1 | 1/2013 | Sullivan et al. | |
| 2013/0096611 A1 | 4/2013 | Sullivan | |
| 2013/0103083 A1 | 4/2013 | Baird | |
| 2013/0144334 A1 | 6/2013 | Bouduban et al. | |
| 2013/0267998 A1 | 10/2013 | Vijay et al. | |
| 2014/0214152 A1 | 7/2014 | Bielefeld | |
| 2015/0080972 A1* | 3/2015 | Chin | A61B 17/1655 |
| | | | 606/304 |

FOREIGN PATENT DOCUMENTS

| | | |
|---|---|---|
| WO | 2000030552 A1 | 6/2000 |
| WO | 2002005718 A1 | 1/2002 |
| WO | 2013114347 A1 | 8/2013 |
| WO | 1997029693 A1 | 1/2014 |
| WO | 2014018946 A1 | 1/2014 |
| WO | 2014189605 A1 | 11/2014 |

OTHER PUBLICATIONS

Suture anchor HITCH, downloaded from www.medicalexpo.com on Oct. 18, 2013.
Invitation to Pay Additional Fees for related International Application No. PCT/US2015/065287 dated Mar. 16, 2016.
Invitation to Pay Additional Fees for related International Application No. PCT/US2015/065203 dated Mar. 16, 2016.
Invitation to Pay Additional Fees for related International Application No. PCT/US2015/065212 dated Mar. 16, 2016.
International Search Report and Written Opinion from related International Application No. PCT/US2015/065287 dated May 31, 2016.
International Search Report and Written Opinion from related International Application No. PCT/US2015/065203 dated May 24, 2016.
International Search Report and Written Opinion from related International Application No. PCT/US2015/065212 dated May 30, 2016.
International Preliminary Report on Patentability from related PCT Application No. PCT/US2015/065203 dated Jun. 13, 2017.
International Preliminary Report on Patentability from related PCT Application No. PCT/US2015/065287 dated Jun. 13, 2017.
International Preliminary Report on Patentability from related PCT Application No. PCT/US2015/065212 dated Jun. 13, 2017.
Chinese Application No. 201580067336.2 First Office Action dated Oct. 26, 2018.
Chinese Search Report for Application No. 201580067336.2.
European Search Report for Application No. 19161652.3-1122 dated Aug. 5, 2019.
Notice of Reasons for Rejection Office Action—Application No. 2017-531221 dated Aug. 26, 2019.
Australian Examination Report for Application No. 2015360315 dated Aug. 23, 2019.
Chinese Second Office Action—Application No. 201580067336.2 dated Aug. 21, 2019.
Chinese Search Report—Application No. 201580067336.2.
Office action issued in corresponding Chinese application No. 201580067336.2 dated Mar. 30, 2020.
Search report issued with office action in corresponding Chinese application No. 20150067336.2 dated Mar. 30, 2020.
Office action issued in corresponding Japanese application No. 2017-531221 dated Feb. 17, 2020.

* cited by examiner

BONE ANCHOR HAVING IMPROVED FIXATION STRENGTH

BACKGROUND

Bone anchors are often used in surgical procedures for fixation. For example, an anchor may be attached to a suture and implanted into bone. After implantation into bone, the anchor engages the bone and resists further movement, providing an anchor point for the attached suture.

The fixation strength of the anchor to the bone is determined by the area of contact between the bone and the anchor and the normal force present there between (i.e., frictional sliding resistance). Assuming a constant normal force, as the contact area is increased, the fixation strength generally increases and vice versa.

In recent years, however, surgeons have been moving towards the use of smaller anchors in surgical repair operations. For example, the use of smaller anchors may be less invasive and allow for more rapid patient healing. With the user of smaller suture anchors, less surface area is available for frictional engagement with the surrounding bone and, thus, lower fixation strength is observed.

Accordingly, as the size of suture anchors decrease, there is a need for improved anchor designs that preserve and/or increase fixation strength with bone when implanted.

SUMMARY

In an embodiment, a suture anchor is provided. The suture anchor includes a generally elongated anchor body extending from a proximal end to a distal end along a longitudinal axis, where a distal portion of the anchor body is tapered. The suture anchor further includes an eyelet formed through the anchor body, extending transverse to the longitudinal axis, and dimensioned to receive a suture, a plurality of first channels formed within the outer surface of the anchor body and extending longitudinally along at least a portion of the anchor body, and a plurality of circumferentially spaced ribs defined between the first channels and extending longitudinally along at least a portion of the anchor body length, where a distal end of each rib terminates within the tapered distal portion of the anchor body.

In further embodiments, the suture anchor includes one or more of the following, in any combination.

In an embodiment of the suture anchor, a height of at least two of the plurality of ribs is different.

In an embodiment, the suture anchor further includes a plurality of second channels formed within the surface of the anchor body and extending proximally from the eyelet.

In an embodiment of the suture anchor, each of the plurality of ribs extends distally past the eyelet.

In an embodiment of the suture anchor, a midline of each of the plurality of ribs is separated by an angle selected between about 7 degrees to about 60 degrees.

In an embodiment of the suture anchor, a ratio of height to width of each of the plurality of ribs is selected within the range between about 1:4 to about 20:1.

In an embodiment of the suture anchor, a ratio of the anchor body diameter to the height of each of the plurality of ribs is selected within the range between about 1:2 to about 1:10.

In an embodiment of the suture anchor, the tapered distal portion of the anchor body is selected within the range between about 10% to about 30% of the total anchor body length.

In an embodiment of the suture anchor, a distal terminus of the anchor body is blunt.

In an embodiment of the suture anchor, a distal terminus of the anchor body is sharp.

In an embodiment of the suture anchor, each of the plurality of ribs tapers towards the radial direction and wherein.

In an embodiment of the suture anchor, each of the plurality of ribs radially tapers to a vertex.

In an embodiment of the suture anchor, the anchor body possesses a root mean squared (RMS) surface roughness greater than or equal to 2 micro inches.

In an embodiment, a kit is provided. The kit includes an embodiment of the suture anchor discussed above and at least one of an awl and a drill having a diameter approximately equal to a diameter of the anchor body.

In an embodiment, a suture anchor is provided. The suture anchor includes a generally elongate anchor body core extending from a proximal end to a distal end along a longitudinal axis, where at least a distal end of the anchor body core is tapered. The suture anchor further includes an eyelet formed through the anchor body, extending transverse to the longitudinal axis, and dimensioned to receive a suture and a plurality of circumferentially spaced ribs extending radially outward from the anchor body core, where each of the plurality of ribs extends longitudinally along at least a portion of the anchor body length. A proximal portion of each rib extends proximal to the tapered distal end of the anchor body core, where a distal portion of each of the plurality of ribs is tapered and terminates within the tapered distal end of the anchor body core and where a taper angle of the distal end of each the plurality of ribs is greater than the taper angle of the distal end of the anchor body core.

Embodiments of the suture anchor may include one or more of the following, in any combination.

In an embodiment of the suture anchor, a distal leading edge of each of the plurality of ribs is formed in a knife-edge configuration.

In an embodiment, the suture anchor further includes a plurality of channels formed on the surface of the anchor body core and extending proximally from the eyelet, wherein the width of each channel is dimensioned to receive a suture.

In an embodiment of the suture anchor, the circumferential spacing between each of the plurality ribs is selected within the range between about 7 degrees to about 60 degrees.

In an embodiment of the suture anchor, a ratio of height to width of each of the plurality of ribs is selected within the range between about 1:4 to about 20:1.

In an embodiment of the suture anchor, a ratio of the anchor body diameter to the height of each of the plurality of ribs is selected within the range between about 1:2 to about 1:20.

In an embodiment of the suture anchor, the tapered distal portion of the anchor body is selected within the range between about 10% to about 30% of the total anchor body length.

In an embodiment of the suture anchor, the taper angle of the distal portion of each of the plurality of ribs is selected within the range between about 25 degrees to about 45 degrees.

In an embodiment of the suture anchor, the taper angle of the distal end of the anchor body core is selected within the range between about 5 degrees to about 25 degrees with respect to the longitudinal axis.

In an embodiment, a kit is provided. The kit includes an embodiment of the suture anchor discussed above and at least one of an awl and a drill having a diameter approximately equal to the diameter of the anchor body core.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1A:
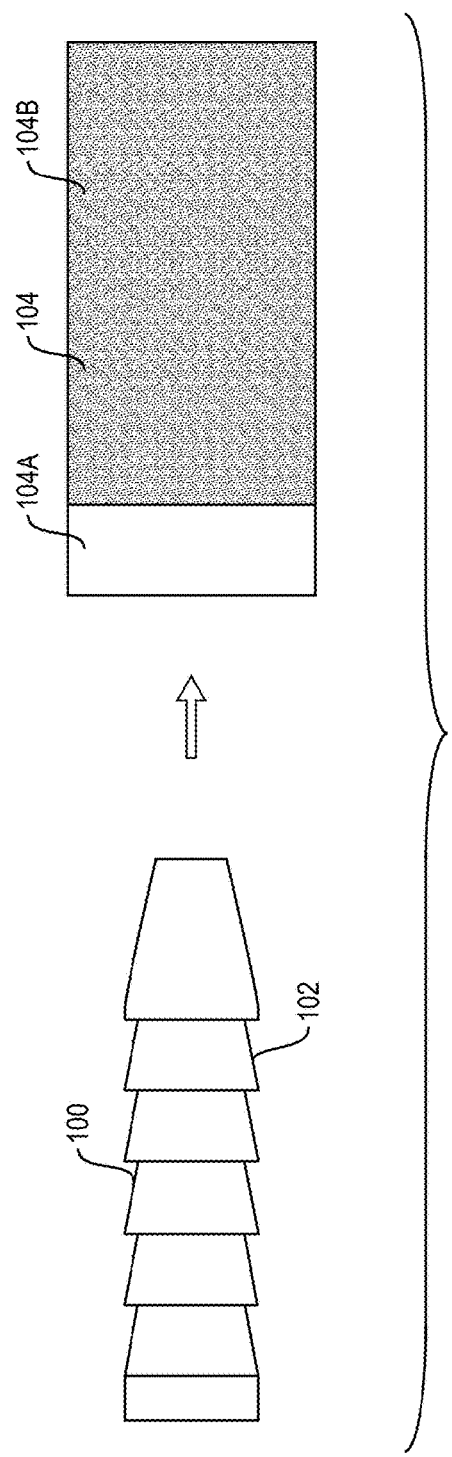
FIGS. 1A-1B are schematic illustrations of a conventional bone anchor, including circumferential ribs, inserted into a bone, demonstrating plow-out of surrounding bone material.
Figure 1B:
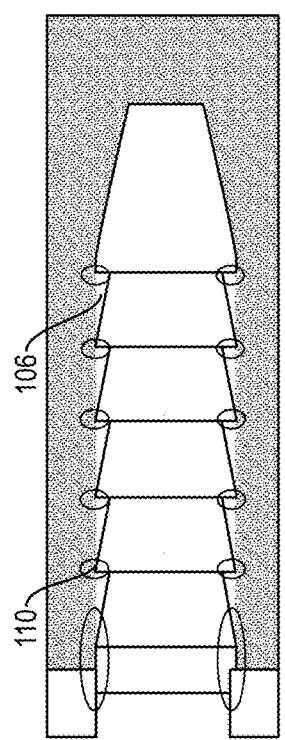

With reference to FIGS. 1A-1B, insertion of a conventional bone anchor 100 into bone 104 is illustrated. In order to enhance the fixation strength of bone anchors, protruding features, such as circumferential ribs 102, are often added to the bone anchor 100 to enhance frictional engagement between the bone anchor 100 upon insertion into the bone 104. However, owing to the porous structure of the bone 104, particularly the soft cancellous bone 104B lying beneath the outer cortical bone layer 104A, upon insertion of the anchor 100, the cancellous bone 104B does not deform elastically (i.e., reversibly) to accommodate the anchor. Instead, these protruding features 102 compact bone material within their wake, creating void space 106 between the anchor body and the surrounding bone, referred to as a "plow-out" effect. As a consequence, the extent of contact between the anchor and the bone 104 is limited to certain contact points 110 at the outer periphery of the bone anchor 100, rather than the entire surface of the bone anchor 100. Accordingly, the degree of fixation achieved by existing bone anchor designs, such as that of bone anchor 100, may fail to achieve desired levels of fixation for a given anchor size.

Embodiments of the present disclosure are directed to bone anchors having improved fixation as compared to conventional bone anchors. For example, as discussed in greater detail below, embodiments of the disclosed bone anchors including an anchor body having a tapered distal end and ribs extending longitudinally along at least a portion of the length of the anchor. The plurality of ribs further extend between the anchor body and the tapered distal tip, where the distal portion of the rib terminates within the tapered distal tip. Such ribs mitigate the plow-out effect, preserving contact between the ribs and the surrounding bone along the length of the anchor and providing increased surface area contact with the bone, improving fixation strength.

In certain embodiments, the ribs are defined by longitudinal channels formed in the anchor body surface. In other embodiments, the ribs extend radially outward from the anchor body surface. In further embodiments, the leading distal edge of the ribs are configured in a tapered "knife-edge" configuration, allowing the distal end of the anchor to cut through the bone more efficiently.

Figure 2A:
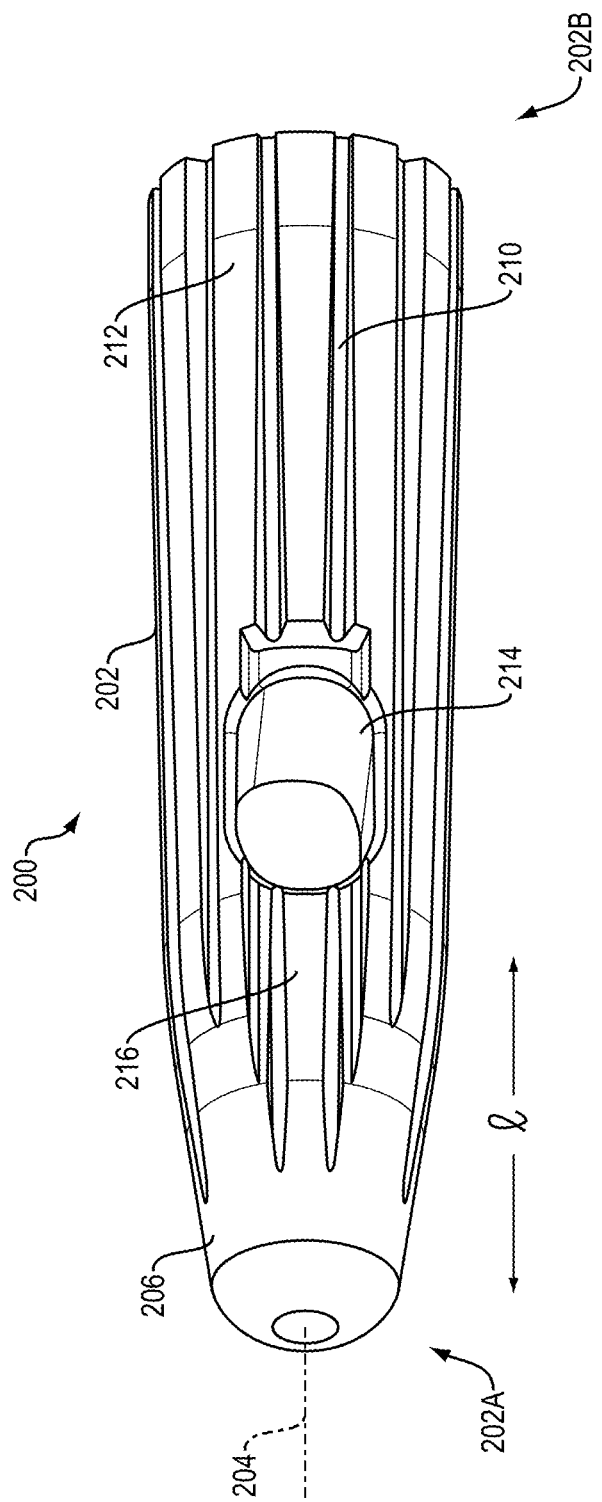
FIGS. 2A-2C are schematic illustrations of embodiments of an improved bone anchor of the present disclosure including longitudinal ribs.
Figure 2B:
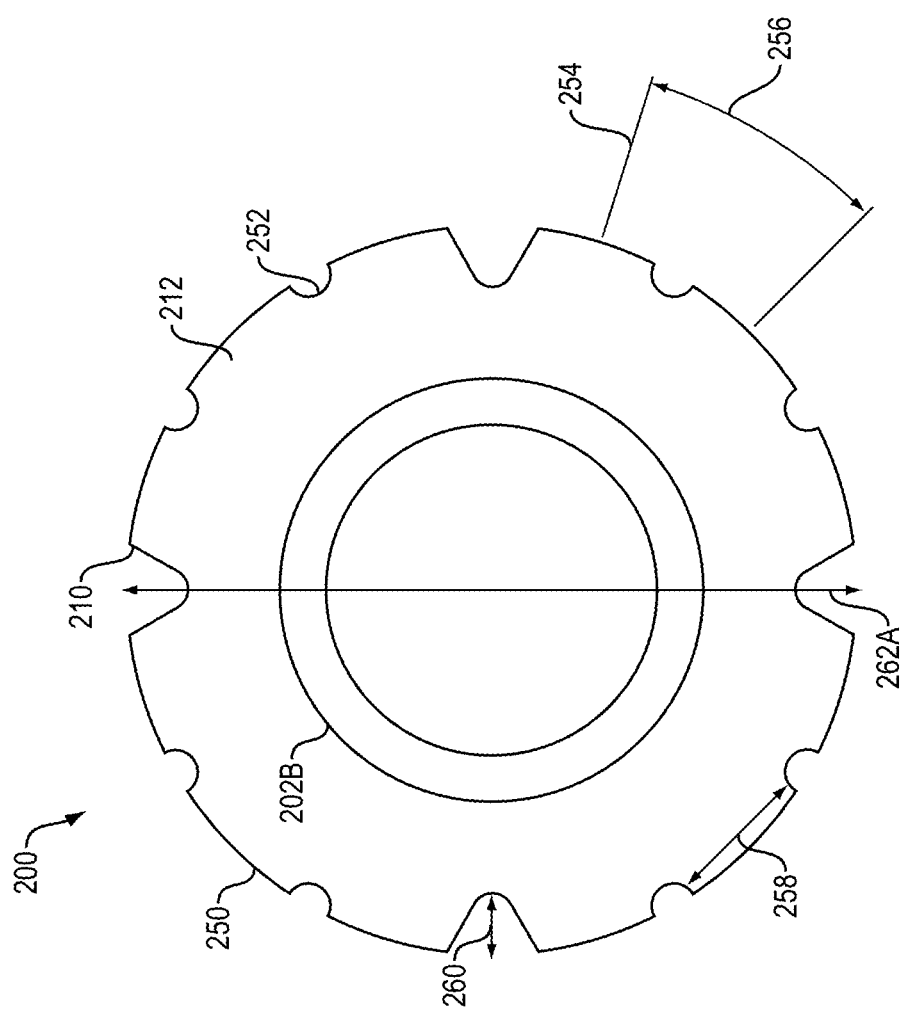
Figure 2C:
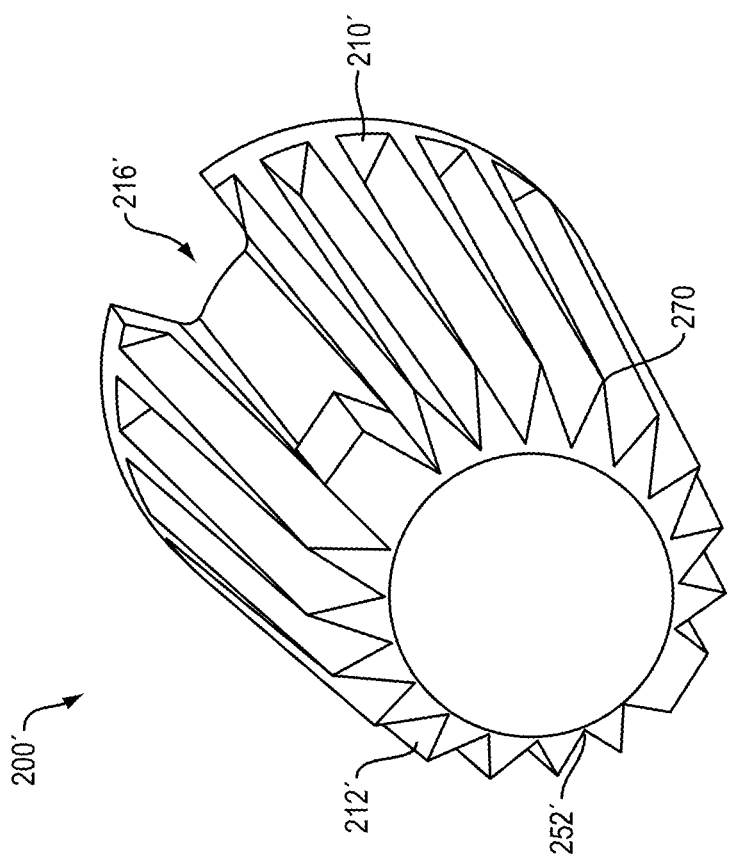

The discussion will now turn to the embodiment of FIGS. 2A-2C, which illustrate embodiments of bone anchors of the present disclosure. Side and end-on views of a first bone anchor embodiment 200 are illustrated in FIGS. 2A-2B, respectively. A second bone anchor embodiment 250 is illustrated in FIG. 2C in a perspective, end-on view.

With reference to FIGS. 2A-2B, the bone anchor 200 includes a generally elongated anchor body 202 extending from a distal end 202A to a proximal end 202B along a longitudinal axis 204. The proximal end 202B of the anchor 200 is adapted to engage a tool for positioning and insertion of the anchor 200 into a bone. For example, in certain embodiments (not shown), the proximal end may include an aperture for receipt of an inserter tool. In other embodiments, the proximal end may be adapted for insertion within an inserter tool.

The distal end 202A of the anchor body 202 is further adapted for insertion into bone. For example, as illustrated in FIG. 2A, the distal end 202A of the anchor body 202 includes a tapered portion 206. In certain embodiments, a length, l, of the taper 206 ranges between about 10% to about 30% of the total length of the anchor body 202. In other embodiments, the taper may extend along greater portions of the anchor body length, up to and including the entire length. In further embodiments, the tapered distal portion of the anchor body may terminate in a selected geometry. Examples may include, but are not limited to, a generally flat tip (e.g., extending approximately perpendicular to the longitudinal axis), a rounded tip, a sharp tip, and configurations there between.

The anchor body 202 further includes a suture eyelet 214. The eyelet 214 extends through the anchor body 202, transverse to its longitudinal axis 204, and is dimensioned to receive a suture. For example, a suture (not shown) may be routed through the eyelet, with free limbs extending adjacent the outer surface of the anchor body. In alternative embodiments, the eyelet may include a bar or other protrusion for securing a suture thereto. In further alternative embodiments, the anchor body is cannulated and suture may be routed through the cannulation, and secured to the bar or protrusion.

With reference to FIG. 2B, the anchor body 202 further includes a plurality of first channels 210 formed in the outer surface 250 of the anchor body 202. Each of the channels 210 includes a channel root 252. In certain embodiments, the channels 210 possess a curved channel root 252 (e.g., ovoid or circular) transitioning into generally curved or straight sides moving towards the outer surface 250 of the anchor body 202.

The first plurality of channels 210 define a plurality of ribs 212 there between that are circumferentially spaced about the anchor body 202. For example, as illustrated in FIG. 2B, the plurality of ribs 212 so defined extend radially outward and terminate at the outer surface of the anchor body 202.

In alternative embodiments of the anchor 200', illustrated in FIG. 2C, a first plurality of channels 210' define a plurality of ribs 212' there between that are circumferentially spaced about the anchor body 202. For example, each of the plurality of ribs 212' terminates in a vertex 270. The vertex may be positioned at the outer surface of the anchor body or a position radially inward there from.

In further embodiments, illustrated in FIG. 2C, the anchor 200' includes a second plurality of channels 216'. The plurality of second channels 216' are formed in the surface of the anchor body 200' and extend proximally from the eyelet. A width of each second channel 216' is dimensioned to receive a suture therein.

The cross-sectional area of each of the plurality of ribs 212, 212' is further defined by the channels 210, 210', respectively. For example, as illustrated in FIG. 2B, at least a portion of plurality of channels 210 possess a curved (e.g., a semi-circular cross-section). In further embodiments, at least a portion of the plurality of channels 210' possess a combination of curved and straight sides (e.g., a curved or semi-circular root) transitioning into a straight side. So configured, the plurality of ribs 212 are generally trapezoidal or mesa-like in shape. In additional embodiments, as illustrated in FIG. 2C, the plurality of channels 210' are generally straight sided, having a sharp-tipped root 252', defining ribs 212' terminating in a vertex 270.

In an embodiment, the channels 210, 210' extend along at least a portion of the length of the anchor 200, where a distal end of each rib 212, 212' terminates within the tapered distal portion 206. For example, as illustrated in FIGS. 2A, 2C the ribs 212, 212' extend from about the proximal end of the anchor 202 to within the tapered distal portion 206. However, it may be understood that, in alternative embodiments, a proximal end of the ribs may be positioned at any location proximal to the tapered distal portion and a distal end of the ribs may terminate at any location within the tapered distal portion. Furthermore, while the each of the ribs 212, 212' at a given circumferential position are illustrated as being formed from a single member, in alternative embodiments, a given rib may be formed in multiple, discrete segments.

As further illustrated in FIGS. 2A, 2C, the ribs 212, 212' extend approximately parallel to the longitudinal axis 204. However, in alternative embodiments, at least a portion of the ribs may extend at a selected angle with respect to the longitudinal axis.

In certain embodiments, at least two of the plurality of channels 210, 210' are of different depth. For example, as illustrated in FIG. 2B, the channels 210 may adopt two different depths, in a repeating pattern (e.g., one deep channel, two shallow channels) about the circumference of the anchor body 202. In other embodiments, as illustrated in FIG. 2C, each of the channels 210' may possess approximately the same depth. In further embodiments, the depth of the each of the channels defining the ribs may be independently varied, as necessary.

Viewed end-on, as illustrated in FIG. 2B, additional parameters of the anchor body 202 geometry is defined. It may be understood that, while such geometries may be discussed in the context of FIG. 2B, they may also be applicable to the embodiments of FIG. 2C. For example, a height 260 of a respective rib 212 is defined by the depth of the channels 210 defining the rib 212. Alternatively, in the circumstance that a rib is defined by channels having different depths, the rib height may be given by the average of the depths of its respective defining channels. A width of a respective rib may be given by the average distance between respective lateral walls of the rib. In certain embodiments, a ratio of rib height 260 to rib width 258 is selected within the range between about 1:4 and about 20:1. In further embodiments, an anchor body diameter 262A to rib height 260 is selected within the range between about 1:2 to about 1:10.

The circumferential spacing of the ribs 212 is variable, as necessary, by positioning of the channels. For example, a midline 254 of each rib is taken as the center point along the rib width 252. The rib spacing is defined by an angle 256 between adjacent midlines 254. In certain embodiments, the separation angle is selected between about 7 degrees to about 60 degrees.

Figure 3A:
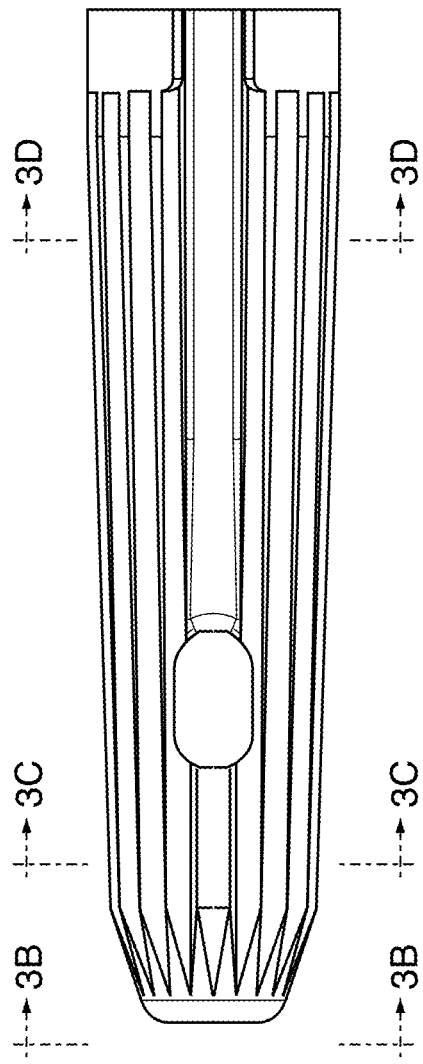
FIGS. 3A-3D are schematic illustrations of the bone anchor of FIGS. 2A-2C upon insertion into bone, demonstrating improved contact area.
Figure 3D:
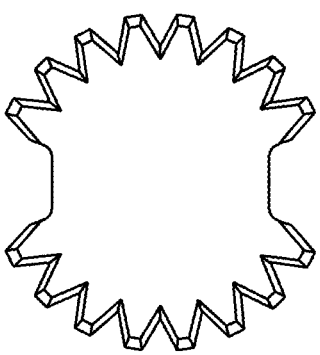
Figure 3C:
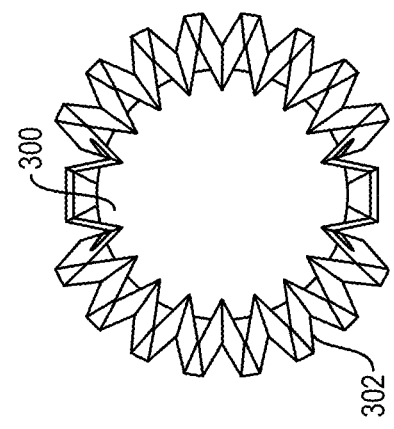
Figure 3B:
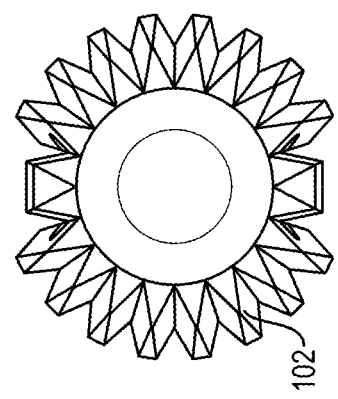

The discussion will now turn to FIGS. 3A-3D, schematically illustrating the portions of the anchor in contact with a bone during insertion. FIG. 3A illustrates an embodiment of the anchor 200' in a side view. FIGS. 3B-3D show corresponding portions of the anchor 200', in cross-section towards the proximal end 202B. The outer periphery of FIGS. 3B-3D represent the outer surface of the anchor body 202'. As the anchor 200 is inserted into the bone, moving in sequence from FIG. 3B-3D, it may be observed that the surface area of the anchor 200' in contact with the bone increases. However, as the channels 210' and ribs 212' are oriented approximately parallel to the longitudinal axis 204, the ribs 212' remain in contact with the surrounding bone about the entirety of their length (i.e., the anchor 200' exhibits minimal plow-out). As further demonstrated below, this enhances the fixation strength of the anchor in bone. Similar observations hold for embodiments of the anchor of FIGS. 2A-2B.

Figure 4A:
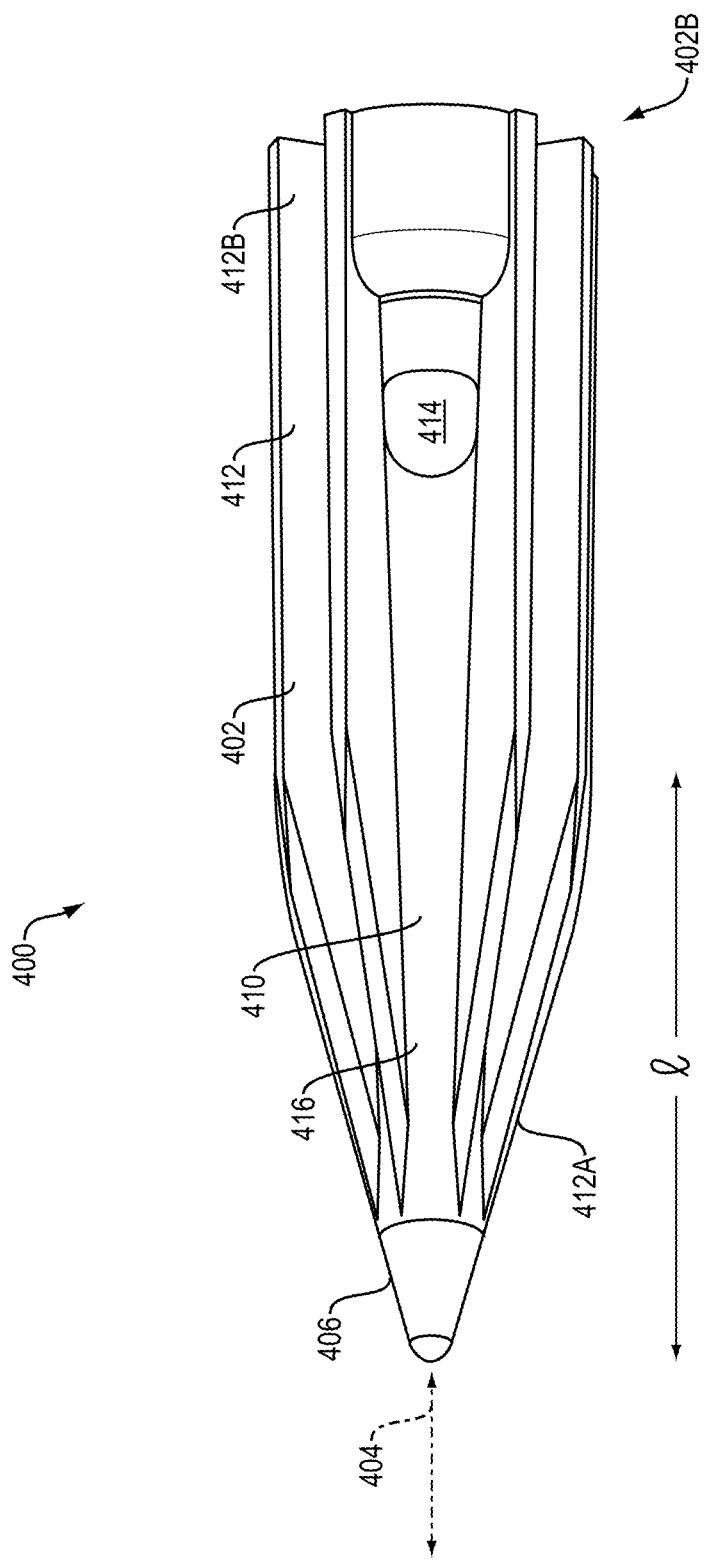
FIGS. 4A-4B are schematic illustrations of another embodiment of an improved bone anchor of the present disclosure including longitudinal ribs.
Figure 4B:
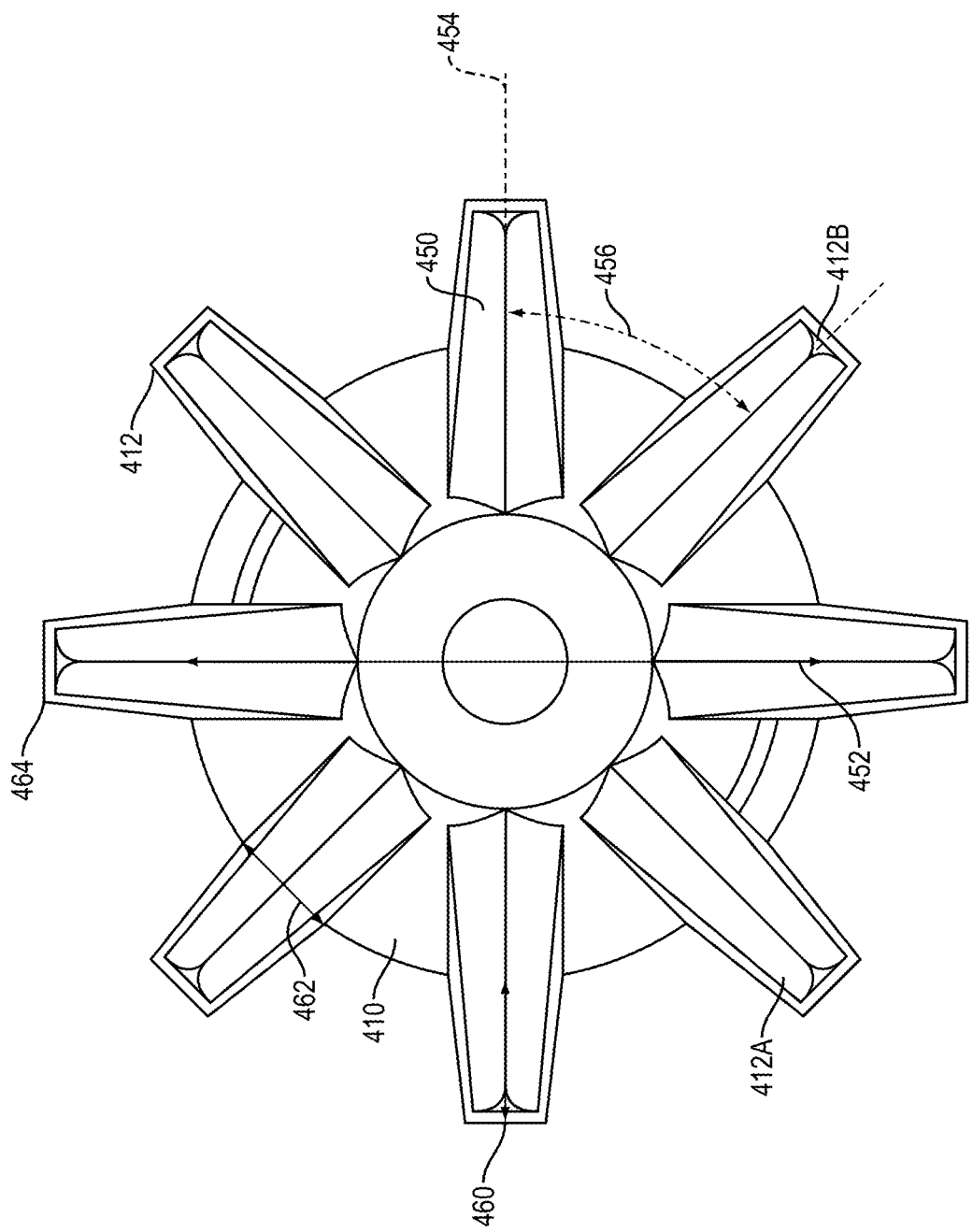

With further reference to FIGS. 4A-4B, side and end-on views of a third bone anchor embodiment 400 are illustrated, respectively. The bone anchor 400 includes a generally elongated anchor body 402 having a core 410 extending from a distal end 402A to a proximal end 402B along a longitudinal axis 404. The proximal end 402B of the anchor 400 is adapted to engage a tool for positioning and insertion of the anchor 400 into a bone. For example, in certain embodiments (not shown), the proximal end may include an aperture for receipt of an inserter tool. In other embodiments, the proximal end may be adapted for insertion within an inserter tool.

The anchor 400 is further adapted for insertion into bone. For example, as illustrated in FIG. 4A, the distal end 402A of the anchor core 410 includes a tapered tip portion 406. In certain embodiments, the length of the tapered portion 406 ranges between about 10% to about 30% of the total length of the anchor core 410. In other embodiments, the taper may extend along greater portions of the anchor body length, up to and including the entire length. In further embodiments, the tapered distal portion of the anchor body may terminate in a selected geometry. Examples may include, but are not limited to, a generally flat tip (e.g., extending approximately perpendicular to the longitudinal axis), a rounded tip, a sharp tip, and configurations there between.

The anchor body 402 further includes a suture eyelet 414. The eyelet 414 extends through the anchor body 402, transverse to the longitudinal axis 404, and is dimensioned to receive a suture. For example, in use, a suture (not shown) may be routed through the eyelet, with free limbs extending adjacent the outer surface of the anchor body. In alternative embodiments, the eyelet may include a bar or other protrusion for securing a suture thereto. In further alternative embodiments, the anchor body is cannulated and suture may be routed through the cannulation, and secured to the bar or protrusion.

In an embodiment, a plurality of channels 416 (e.g., a pair of channels) is also formed in the outer surface of the anchor core 410, extending proximally from proximal ends of the eyelet, approximately parallel to the longitudinal axis 412. A width and depth of the channels 416 is dimensioned to receive a suture therein. In alternative embodiments, the channels may be omitted.

With reference to FIG. 4B, the anchor body 402 further includes a plurality of ribs 412 extending radially outward from, and circumferentially spaced about, the anchor core 410. Each of the plurality of ribs 412 includes a distal rib portion 412A and a proximal rib portion 412B. The distal portion 412A of each of the plurality of ribs 412 is tapered and terminates within the tapered distal end 406 of the anchor body core 410. The proximal rib portion 412B extends proximal to the tapered distal end 412B and is not tapered towards the core 410. However, in alternative embodiments, the proximal rib portion may possess a selected taper, as necessary.

As illustrated in the embodiment of FIG. 4A, the ribs 412 extend from about the proximal end of the anchor 402 to within the tapered distal portion 406. However, it may be understood that, in alternative embodiments, a proximal end of the ribs may be positioned at any location proximal to the tapered distal portion and a distal end of the ribs may terminate at any location within the tapered distal portion.

As further illustrated in FIG. 4A, the plurality of ribs 412 extends along at least a portion of the length of the anchor core 410, approximately parallel to the longitudinal axis 404. However, in alternative embodiments, at least a portion of the ribs may extend at a selected angle with respect to the longitudinal axis. Furthermore, while the each of the ribs 212, 212' at a given circumferential position are illustrated as being formed from a single member, in alternative embodiments, a given rib may be formed in multiple, discrete segments.

In further embodiments, a rib taper angle of the distal rib portion 412A is greater than a taper angle of the core 410. For example, the rib taper angle may be selected within the range between about 25 degrees to about 45 degrees, while the core taper angle may be selected within the range between about 5 degrees to about 25 degrees.

In further embodiments, a leading distal edge of the tapered portion 412A of the ribs 412 may include laterally tapered surfaces. This lateral taper, also referred to as a "knife edge" configuration, facilitates insertion of the ribs 412 into bone by gradually increasing the surface area of each rib in contact with the bone. As a result, the structurally intact bone surrounding the anchor is able to generate a greater reaction force against the surface of the inserted anchor. This greater reaction force in turn translates into increased contact pressure which in turn translates into increased anchor fixation strength.

Viewed end-on, as illustrated in FIG. 4B, additional parameters of the anchor body 202 geometry are defined. For example, a height 460 of a respective rib is defined by the radial distance that the rib extends beyond the anchor core 410. A width 462 of a respective rib is given by the average distance between respective lateral walls of the rib. In certain embodiments, a ratio of rib height 460 to rib width 462 may be selected within the range between about 1:4 and about 20:1. In further embodiments, an anchor core diameter 452 to rib height 460 may be selected within the range between about 1:2 to about 1:10.

The circumferential spacing of the ribs 412 is also variable, as necessary. For example, a midline 454 of each rib may be taken as the center point along the rib width 462. The rib spacing may be defined by an angle 456 between adjacent midlines 454. In certain embodiments, the separation angle may be selected between about 7 degrees to about 60 degrees.

Figure 5A:
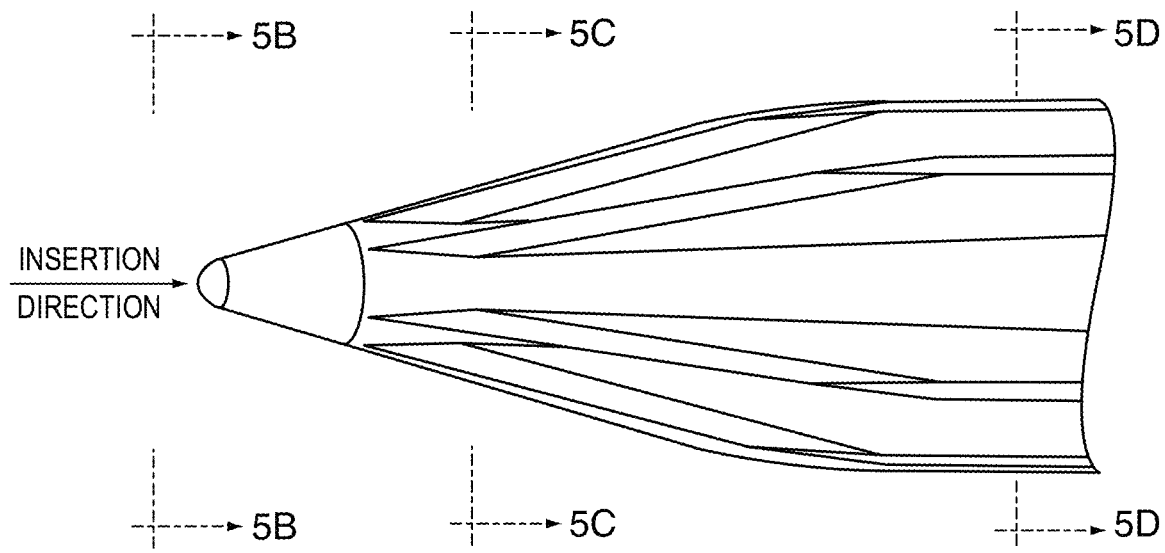
FIGS. 5A-5D are schematic illustrations of the bone anchor of FIGS. 4A-4B upon insertion into bone, demonstrating improved contact area.
Figure 5B:
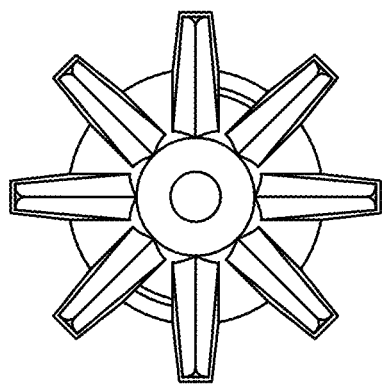
Figure 5C:
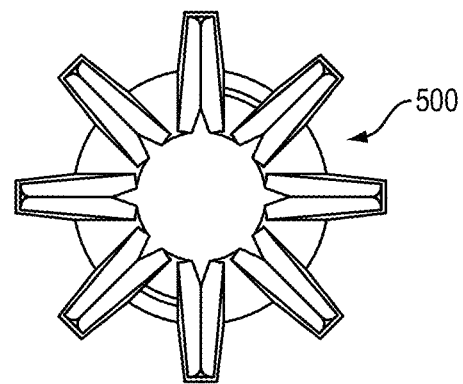
Figure 5D:
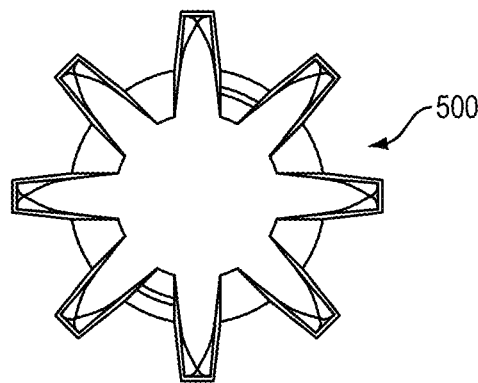

The discussion will now turn to FIGS. 5A-5D, schematically illustrating the portions of the anchor 400 in contact with a bone during insertion. FIG. 5A illustrates an embodiment of the anchor 400 in side view. FIGS. 5B-5D illustrate corresponding portions of the anchor 400 in cross-sections towards the proximal end 402B. The outer periphery of FIGS. 5B-5D represent the outer surface of the anchor body 202. As the anchor 400 is inserted into the bone, moving in sequence from FIG. 5B-5D, it may be observed that the surface area of the anchor 400 in contact with the bone gradually increases. However, as the channels 410 and ribs 412 are oriented approximately parallel to the longitudinal axis 404, the ribs 412 remain in contact with the surrounding bone about the entirety of their length (i.e., the anchor 400 exhibits minimal plow-out). As further demonstrated below, this enhances the fixation strength of the anchor in bone.

Figure 6A:
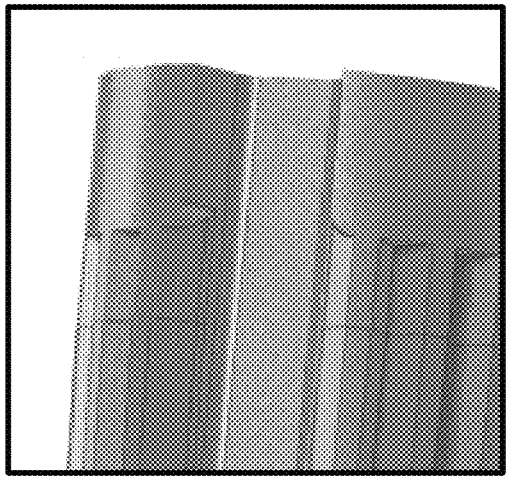
FIGS. 6A-6D are schematic illustrations of embodiments of surface textures for use with embodiments of the bone anchors of FIGS. 2A-2C and 4A-4B.
Figure 6B:
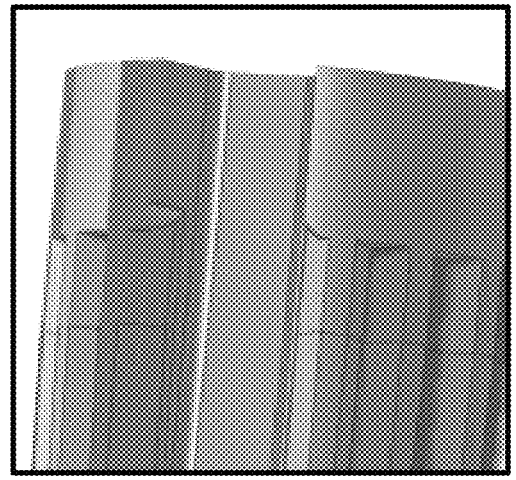
Figure 6C:
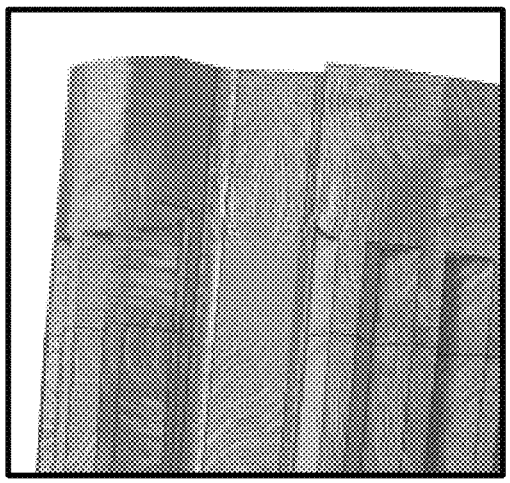
Figure 6D:
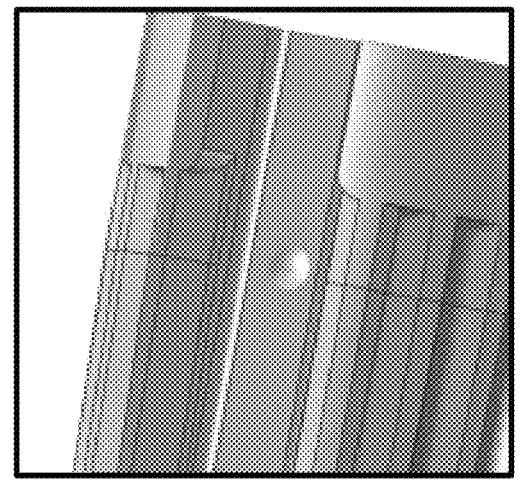

In further embodiments, the fixation strength of embodiments of the disclosed anchors (e.g., 200, 200', 400) are enhanced by texturing the outer surface. For example, as illustrated in FIGS. 6A-6D. Surface textures may be achieved through techniques including, but not limited to, sandblasting (FIG. 6A), brushing (FIG. 6B), burnishing (FIG. 6C), and dimpling (FIG. 6D). In certain embodiments, such texturing may provide embodiments of the anchor with a surface roughness having a root mean squared (RMS) value greater than or equal to about 2 micro inches.

To examine the fixation strength of embodiments of the anchor discussed herein, as compared to existing suture anchors, pullout tests were performed. Each anchor possessed a diameter of 5.5 mm. A first comparative suture anchor, possessed circumferential ribs and was tested 5 times. A second comparative suture anchor possessed laterally protruding wings and was tested 5 times. A third comparative suture anchor possessed helical threads and was tested 20 times. An embodiment of the suture anchor 400 of FIGS. 4A-4B was further tested 5 times. Each anchor possessed a diameter of 5.5 mm.

Figure 7:
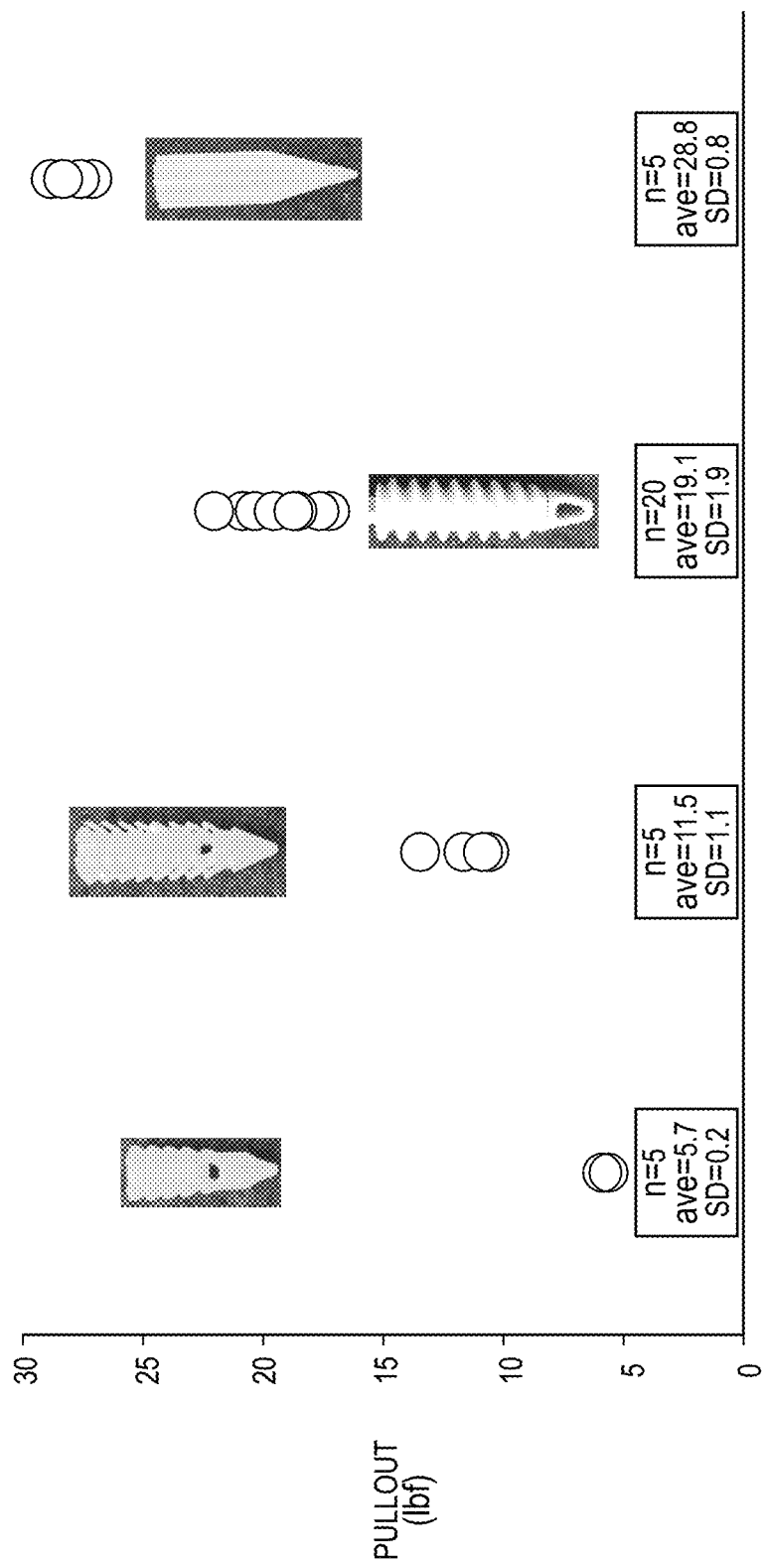
FIG. 7 is a plot of fixation strength measured for different bone anchors including embodiments of the present disclosure.

It may be observed from the plot of FIG. 7 that embodiments of the anchor 400, disclosed herein exhibited significantly improved fixation strength, as measured in pullout. For example, embodiments of the disclosed anchor were measured to have a pullout strength of 28.8 lbf, with a standard deviation of 0.8, while the pullout strength measured for the Comparative Anchors 1-3 ranged between about 5.7 lbf to about 19.1 lbf.

Figure 8B:
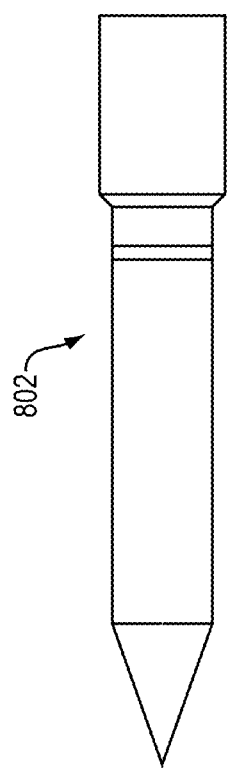
FIGS. 8A-8D are schematic illustrations of embodiments of awls for use in preparing pilot holes for embodiments of corresponding bone anchors of the present disclosure.
Figure 8D:
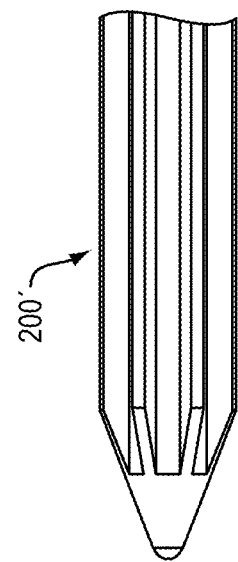
Figure 8A:
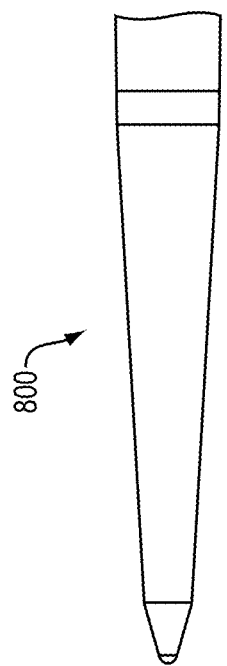
Figure 8C:
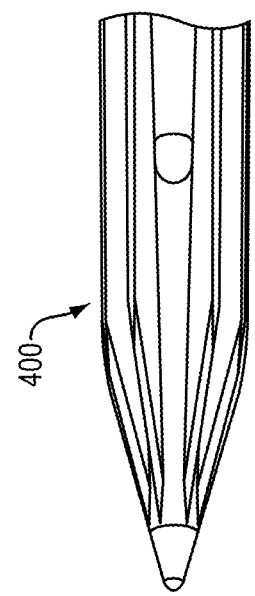

FIGS. 8A-8B illustrate embodiments of hole preparation devices 800, 802 for use in combination with embodiments of the suture anchors (e.g., 200, 200', 400) discussed above. A profile of the hole preparation device 800, 802 (e.g., an awl or drill) is matched with the anchor body or anchor core diameter (as appropriate). This is in contrast to existing approaches, which employ hole preparation devices that possess a profile of minimum size needed to successfully insert the anchor into hard bone. In contrast, by employing the hole preparation devices 800, 802 matched to the size of anchor diameter, the amount of force required to insert the anchor into bone is reduced to the greatest degree possible while still accommodating the cross-section of the anchor body or core within the prepared bone hole.

This force reduction improves the likelihood that, during insertion, the structural integrity of bone adjacent to the anchor is maintained. With the integrity of the bone adjacent to the anchor preserved, in combination with the increased contact area, between the anchor and bone maximized, fixation strength is further improved.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A suture anchor for insertion into bone, comprising:
   a generally elongated anchor body extending from a proximal end to a distal end along a longitudinal axis, wherein a distal portion of the anchor body is tapered toward a tip;
   an eyelet formed through the anchor body, extending transverse to the longitudinal axis, and dimensioned to receive a suture;
   a plurality of first channels formed within an outer surface of the anchor body and extending from a region proximal to the eyelet distally along at least a portion of the anchor body, adjacent sides of each of the plurality of first channels sharing a sharp-tipped root, the adjacent sides of each of the plurality of first channels being straight from the shared root to a vertex along an entire length of the first channels;
   a plurality of second channels formed within the outer surface of the anchor body and extending proximally from the eyelet, a width of the second channels selected to be greater than a width of the first channels and dimensioned to receive a suture; and
   a plurality of circumferentially spaced ribs defined between the first channels;
   wherein a diameter of the anchor body at any fixed point along a length of the anchor body does not expand radially;
   wherein a cross-sectional area of the anchor body increases from the distal end to the proximal end such that a surface area of the anchor body in contact with bone increases from the distal end to the proximal end; and
   wherein the proximal end of the body is adapted for insertion within an inserter tool.

2. The suture anchor of claim 1, wherein a height of at least one of the plurality of ribs not interrupted by the eyelet is different from a height of another one of the plurality of ribs not interrupted by the eyelet.

3. The suture anchor of claim 1, wherein each of the plurality of ribs extends distally past the eyelet.

4. The suture anchor of claim 1, wherein a midline of each of the plurality of ribs is separated by an angle selected to be between about 7 degrees to about 60 degrees.

5. The suture anchor of claim 1, wherein a ratio of height to width of each of the plurality of ribs is selected to be between about 1:4 to about 20:1.

6. The suture anchor of claim 1, wherein a ratio of a diameter of the anchor body to a height of each of the plurality of ribs is selected to be between about 1:2 to about 1:10.

7. The suture anchor of claim 1, wherein a length of the tapered distal portion of the anchor body is selected to be between about 10% to about 30% of the length of the anchor body.

8. The suture anchor of claim 1, wherein the tip of the anchor body is blunt.

9. The suture anchor of claim 1, wherein the tip of the anchor body is sharp.

10. The suture anchor of claim 1, wherein each of the plurality of ribs tapers towards a radial direction.

11. The suture anchor of claim 1, wherein each of the plurality of ribs radially tapers to the vertex.

12. The suture anchor of claim 1, wherein the anchor body possesses a root mean squared (RMS) surface roughness greater than or equal to 2 micro inches.

13. A kit comprising:
    the suture anchor of claim 1; and
    at least one of an awl and a drill having a diameter approximately equal to a diameter of the anchor body.

14. A suture anchor for insertion into bone, comprising:
    a generally elongate anchor body extending from a proximal end to a distal end along a longitudinal axis, wherein at least a distal end of the anchor body is tapered;
    an eyelet formed through the anchor body, extending transverse to the longitudinal axis, and dimensioned to receive a suture;
    a plurality of first channels formed within an outer surface of the anchor body and extending from a region proximal to the eyelet distally along at least a portion of the anchor body, adjacent sides of each of the plurality of first channels sharing a sharp-tipped root, the adjacent sides of each of the plurality of first channels being straight from the shared root to a vertex along an entire length of the first channels;
    a plurality of second channels formed within the outer surface of the anchor body and extending proximally from the eyelet, a width of the second channels selected to be greater than a width of the first channels and dimensioned to receive a suture; and
    a plurality of circumferentially spaced ribs extending radially outward from the anchor body, wherein each of the plurality of ribs extends from a region proximal to the eyelet distally along at least a portion of a length of the anchor body;
    wherein a diameter of the anchor body at any fixed point along a length of the anchor body does not expand radially;
    wherein a cross-sectional area of the anchor body increases from the distal end to the proximal end such that a surface area of the anchor body in contact with bone increases from the distal end to the proximal end;
    wherein a proximal portion of each rib extends proximal to the tapered distal end of the anchor body;
    wherein the proximal end of the body is adapted for insertion within an inserter tool;
    wherein a distal portion of each of the plurality of ribs is tapered toward a tip of the anchor body; and wherein a taper angle of the distal portion of each of the plurality of ribs is greater than a taper angle of the distal end of the anchor body.

15. The suture anchor of claim 14, wherein a distal leading edge of each of the plurality of ribs is formed in a knife-edge configuration.

16. The suture anchor of claim 14, wherein a circumferential spacing between each of the plurality ribs is selected to be between about 7 degrees to about 60 degrees.

17. The suture anchor of claim 14, wherein a ratio of height to width of each of the plurality of ribs is selected to be between about 1:4 to about 20:1.

18. The suture anchor of claim 14, wherein a ratio of a diameter of the anchor body to a height of each of the plurality of ribs is selected to be between about 1:2 to about 1:20.

19. The suture anchor of claim 14, wherein a length of the tapered distal portion of the anchor body is selected to be between about 10% to about 30% of the length of the anchor body.

20. The suture anchor of claim 14, wherein the taper angle of the distal portion of each of the plurality of ribs is selected to be between about 25 degrees to about 45 degrees with respect to the longitudinal axis.

21. The suture anchor of claim 20, wherein the taper angle of the distal end of the anchor body is selected to be between about 5 degrees to about 25 degrees with respect to the longitudinal axis.

22. A kit comprising:
    the suture anchor of claim 14; and
    at least one of an awl and a drill having a diameter approximately equal to a diameter of the anchor body.

23. The suture anchor of claim 1, wherein a distal portion of each of the plurality of ribs is tapered toward the tip of the anchor body.

24. The suture anchor of claim 1, wherein a pull-out strength of the suture anchor is between 28.0 lbf and 29.6 lbf.

25. The suture anchor of claim 14, wherein a pull-out strength of the suture anchor is between 28.0 lbf and 29.6 lbf.

* * * * *